United States Patent [19]

Dietrich et al.

[11] Patent Number: 4,612,938

[45] Date of Patent: Sep. 23, 1986

[54] METHOD FOR ILLUMINATING CAVITIES

[75] Inventors: Ralph Dietrich; Dieter Jocham, both of Munich; Eberhard Unsöld, Oberschleissheim; Wolfram Weinsheimer; Wolfram Gorisch, both of Munich, all of Fed. Rep. of Germany

[73] Assignee: Gesellschaft für Strahlen- und Umweltforschung mbH, München, Neuherberg, Fed. Rep. of Germany

[21] Appl. No.: 529,853

[22] Filed: Sep. 6, 1983

[30] Foreign Application Priority Data

Sep. 4, 1982 [DE] Fed. Rep. of Germany ....... 3232912
Jun. 29, 1983 [DE] Fed. Rep. of Germany ....... 3323365

[51] Int. Cl.$^4$ ................................................ A61B 6/00
[52] U.S. Cl. .................................. 128/665; 128/303.1; 356/241
[58] Field of Search ............... 128/633, 634, 653, 654, 128/656, 657, 659, 664, 665, 303.1; 362/318, 804; 356/241

[56] References Cited

U.S. PATENT DOCUMENTS

| 1,723,272 | 8/1929 | Emma | 362/318 |
| 4,050,450 | 9/1977 | Polanyi et al. | 128/634 |
| 4,102,582 | 7/1978 | Lord et al. | 356/241 |
| 4,313,431 | 2/1982 | Frank | 128/303.1 |
| 4,383,761 | 5/1983 | Jones | 356/241 |
| 4,449,535 | 5/1984 | Renault | 128/665 |

FOREIGN PATENT DOCUMENTS 0003015 7/1979 European Pat. Off. ............ 128/665

OTHER PUBLICATIONS

Documenta Geigy, Scientific Tables, 1973, pp. 677–678.
Doiro et al, "Fluorescence Bronchoscopy for Detection of Lung Cancer, Chest, 76:1, Jul. 1979, pp. 27–32.
Kinsey et al, "Endoscopic System for Simultaneous Visual Examination and Electronic Detection of Fluorescence", Rev. Sci. Instrum., vol. 51 (10), Oct. 1980, pp. 1403–1406.
Schuette et al, Medical & Biological Engineering, vol. 14, No. 2, pp. 235–238, Mar. 1976.
Kobayashi et al, Journal of Applied Physiology, vol. 31, No. 5, Nov. 1971, pp. 693–696.
J. F. Kelly et al, "Hematoporphyrin Derivative: A Possible . . . ", from *The Journal of Urology*, vol. 115, Feb. 1976, pp. 150–151.

*Primary Examiner*—Kyle L. Howell
*Assistant Examiner*—Ruth S. Smith
*Attorney, Agent, or Firm*—Spencer & Frank

[57] ABSTRACT

The present invention relates to a method and apparatus for the uniform and simultaneous illumination by means of radiation of the interior surfaces of cavities for the purpose of observation and/or irradiation. In particular, such cavities may be not only hollow organ cavities, but also cavities in non-organic objects. The solution provides that the interior of the cavities is filled, at least in part, with a light scattering or dispersing medium and the dispersing medium is caused to shine or scatter light by means of one or a plurality of radiations or scattered light. With the integral irradiation used according to the present invention, two procedures are combined technologically, namely diagnosis and therapy of, for example, carcinoma in organ cavities which have been photosensitized by chemical substances, possibly on the basis of differences in decomposition of cancerous and normal tissue.

16 Claims, 2 Drawing Figures

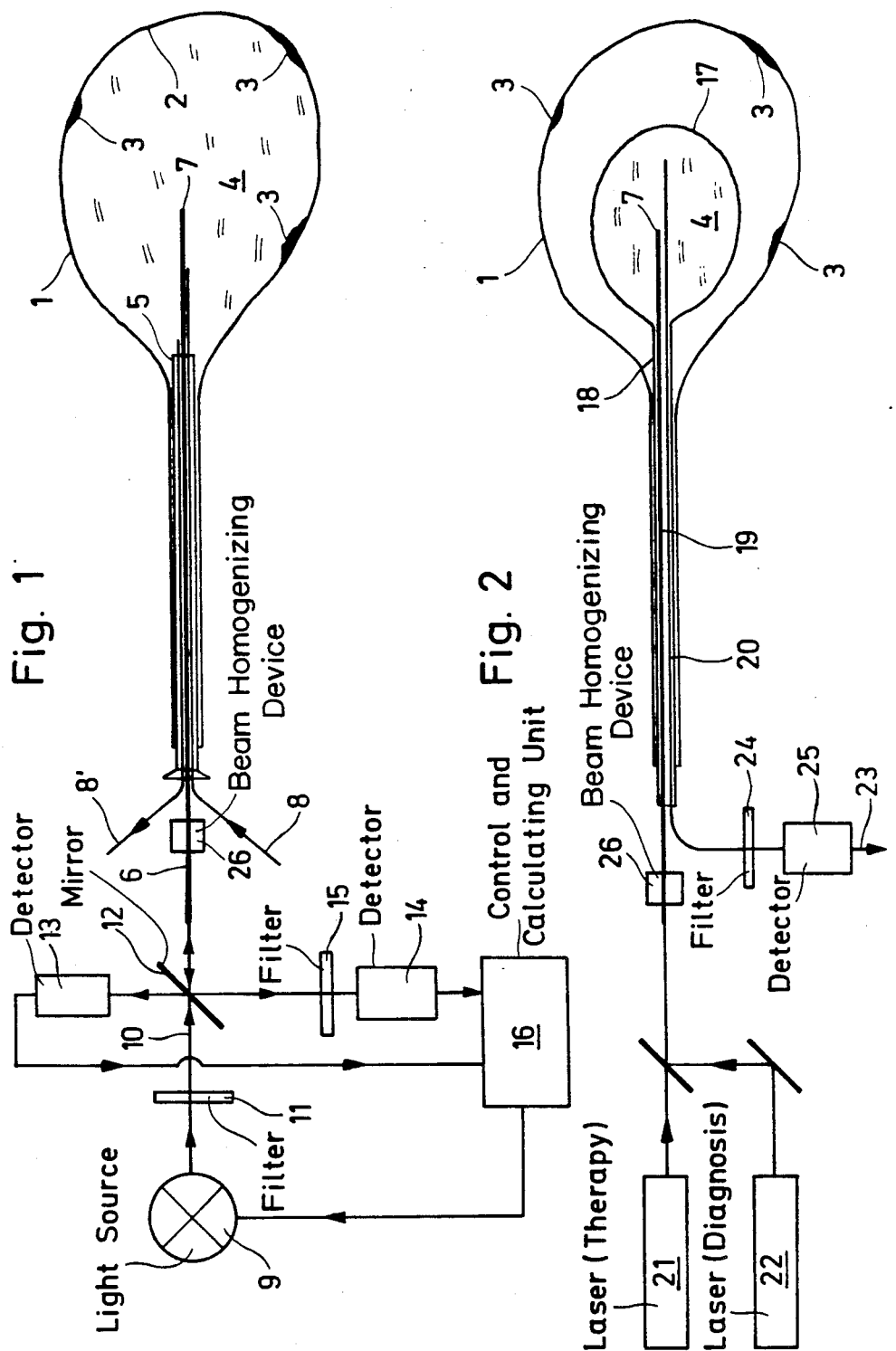

METHOD FOR ILLUMINATING CAVITIES

BACKGROUND OF THE INVENTION

The present invention relates to a method and apparatus for the uniform and simultaneous illumination by means of radiation of the interior surfaces of cavities for the purpose of observing and/or treating the interior surfaces.

In multilocularly growing tumors, e.g. bladder carcinoma, there often exist, in addition to marcroscopically detectable tumor sites, minute microscopic tumor regions. Since it was impossible in the past to detect the latter with conventional therapy procedures (e.g. "Der Urologe" [The Urologist], Edition B, Volume 21, No. 3, June 1981), about 50% of the cases of, for example, bladder carcinoma, manifest themselves within 15 months after first treatment. These are the so-called recurring tumors.

Previously used therapy procedures in connection with bladder carcinoma include transurethral resection, partial bladder resection, and tumor coagulation by means of electrical current or laser radiation (Nd-YAG, argon laser). Local infusion of cell multiplication inhibitors in the bladder have been able to reduce the recurrence rate of surface growing tumors by a maximum of 30%. However, neither the use of local hyperthermia, a procedure that is still in the experimental state, nor the use of ionizing radiation have brought significant improvements.

It is also known (see, e.g., Journal of Urology, Volume 115, February 1976, pages 150–151) to make tumors growing on the interior walls of organ cavities selectively sensitive to light, i.e. to photosensitize them, by dispensing suitable chemical substances, such as hematoporphyrin derivative (HpD), hematoporphyrin, porphyrin, tetracycline, acridine orange, etc. Subsequent irradiation with suitable light, for example red (laser) light for HpD, then leads to photochemical reactions in the photosensitized tissue, resulting ultimately in destruction of the tumor tissues. Normal, nonphotosensitized tissue, however, is not damaged by the low energy light irradiation.

In industry as well, particularly in the motor vehicle construction art, problems arise if cavities that are inaccessible or very difficultly accessible in articles are to be detected, observed and/or irradiated in order to seal them. The same problems exist in the conservation art if, for example, cavities in archeological or historically valuable buildings or articles are to be sealed to protect them against further decay or for reasons of stability.

SUMMARY OF THE INVENTION

It is now the object of the present invention to provide a method with which uniform and simultaneously integral irradiation of the interior surfaces of at least parts of cavities is possible.

The above object is achieved according to the invention by a method for the uniform and simultaneous illumination of the interior surface of a cavity by means of radiation for the purpose of observation and/or treatment of the interior surface comprising the steps of filling the interior of a cavity, at least in part, with a liquid, radiation scattering or dispersing medium, and introducing radiation into the dispersing or scattering medium to cause same to shine or scatter the radiation and perform a uniform and homogeneous illumination or irradiation of the inner wall of the cavity.

The apparatus for carrying out the method basically includes at least one light conductor extending into the cavity and means for producing and/or receiving light connected to the external end of the light conductor.

The integral irradition used according to the present invention makes it possible to perform, in addition to purely technical sealing and conservation processes, two medical procedures, i.e. diagnosis and therapy of, for example, carcinoma in organ cavities, where the carcinoma are photosensitized by chemical substances, possibly on the basis of different types of decay of cancerous and normal tissue, respectively.

The photosensitization can be effected by systematic dispensation or infusion in the respective organ cavity.

The uniform irradiation employed according to the present invention has the advantages that 1. all tumor cells can be therapeutically covered, independently of the fact of whether or not they have been diagnosed completely;
2. measures for aligning the light beam and keeping it constant are no longer required;
3. a catheter to be used need not have an optical viewing system and can therefore be kept thinner so that the stress for the patient and the danger of iatrogenic damage (e.g. strictures) is reduced; and
4. the radiation dosage can be made via the product of energy and time, so that it is possible to employ the required high dosages over long irradiation periods.

In the case of constant visual control of the directed radiation, the duration of the therapy would be limited in practice to within a five-minute range. Integral irradiation, however, permits continuous therapy over periods of time covering many hours.

Therefore, we have here an integral process without cumbersome scanning. The method according to the present invention permits the diagnostic and therapeutic detection of multilocular tumors which cannot be detected or localized visually (carcinoma in situ). The method is not very invasive and can therefore also be used for high risk patients in internal medicine (frequent patient group for such tumors) and can, under certain circumstances, be implemented without anesthesia.

In addition to an improvement in cancer therapy, it can be expected that a reduction in surgical risk and in so-called recurrence rate will occur and connected therewith a significant improvement in the quality of life of bladder cancer patients.

BRIEF DESCRIPTION OF THE DRAWINGS

The present invention will now be explained with the aid of two embodiments relating to medical uses which do not exclude, however, other industrial uses.

FIG. 1 is a schematic illustration of one embodiment of the invention using a single light conductor for conducting light to and from a cavity completely filled with a radiation dispersing liquid medium;

FIG. 2 is a schematic illustration of another embodiment of the invention using separate light conductors for conducting light to and from a cavity which is only partially filled with a radiation dispersing liquid medium.

DETAILED DESCRIPTION OF THE PREFERRED EMBODIMENTS

FIG. 1 shows a bladder as the organ cavity 1 on whose interior walls 2 there are tumor 3. In this embodiment, the interior of organ cavity 1 is filled completely with a liquid light dispersing or scattering medium 4 which may be inserted through a catheter 5 having a continuous outflow 8' and inflow 8 for the dispersing or scattering medium 4. The radiation for treatment of the photosensitized tumors 3 or for purposes of diagnosis is introduced into the organ cavity 1 through a light conductor 6 arranged in the catheter 5. This usually flexible light conductor 6 has an end 7 that is drawn into a point or a sphere and is aligned as centrally as possible in the organ cavity 1. Thus the incoming radiation is able to uniformly excite or irradiate via the scattering or dispersing medium 4, the interior wall 2 of the organ cavity 1 with the tumors 3.

The measuring arrangement for therapy/diagnosis of the tumors includes a therapy or excitation light source 9 which may be, for example, a laser or a mercury ultrahigh pressure lamp, from which light 10, possibly set to a certain wavelength by means of a filter 11, is directed onto light conductor 6. A semitransmissive mirror 12 reflects part of the light 10 from the therapy or excitation light source 9 onto a detector 13 which generates a reference signal from the therapy or excitation light. This reference signal from detector 13 is processed or evaluated in a control and calculating unit 16, together with the measuring signal from a further light detector 14. The detector 14 detects light which is returning from the cavity and which is conducted likewise via the light conductor 6 to mirror 12 where it is reflected onto the detector 14 thorugh a further barrier filter 15. The control unit 16 can, as shown, also control the light source 9 whereby light pulses can be produced which cause fluorescence of the photosensitized tumors 3 and the time curve of this fluorescence can be recorded by the unit 16 for diagnosis purposes. The filter 15 rejects the therapy or excitation light eventually scattered into the measuring channel containing elements 15,14. For diagnostic means using, e.g., Hematoporphyrin-Derivative (HpD), the excitation band of about 405 nm wavelength is obtained by filtering, with interference filters or color glasses, the Hg-lines of 404.7 to 407.8 nm of a high pressure mercury lamp. The fluorescence emission is detected at about 600 nm and therefore the filters 15 (FIG. 1) or 24 (FIG. 2) must be centered at 600 nm while rejecting the eventually scattered excitation light of 405 nm. According to the excitation light, e.g., 405 nm for HpD the dichtoitic mirror 12 must have a passband centered at 405 nm, while reflecting the fluorescence emission at about 600 nm on to the detector 14.

FIG. 2 shows a further possibility for diagnosis/therapy. In this case, the organ cavity 1 is filled only partially with a liquid, light dispersing or scattering medium 4 which is contained in a transparent balloon 17 at the end of a catheter 18 with or without a wire cage. In this embodiment, two light conductors 19 and 20 are introduced separately via the catheter 18 into the dispersing medium 4 within the balloon 17 but only one of the light conductors, i.e. the light conductor 19 is used for irradiation for diagnosis and therapy. Either light from laser 21 (therapy) or from laser 22 (diagnosis) is used for this purpose. The second light conductor 20 serves exclusively to couple out the measuring signal 23 for diagnostic purposes which is conducted to detector 25 via a suitable filter 24. Evaluation and control of therapy/diagnosis are effected corresponding to the embodiment of FIG. 1.

Diagnosis involves the following steps:

(a) homogeneous illumination, by means of the dispersing medium 4, of organ 1 covered with previously photosensitized tumors 3 with light of the excitation wavelength, usually ultraviolet light, of the substance used to photosensitize the tumors; and (b) detection of fluorescence from the tumor regions.

Therapy, on the other hand, involves the following steps:

(a) homogeneous illumination by means of a scattering or dispersing agent 4, which may be different from that used for the diagnosis procedure, with light of the absorption wavelength of the substance used to photosensitize the tumors, e.g. red light for HpD or possibly of another wavelength depending on the substance; and (b) causing phototoxic reactions in the photosensitized regions.

Thus it is possible to employ a routine testing and measuring procedure based on photosensitization in addition to the urin-cytologic cancer test. According to FIGS. 1 and 2, light of suitable excitation wavelengths is conducted through light conductors 6 or 19 respectively, (e.g. laser, gas discharge lamp possibly with filters) and the wall 2 of the organ cavity 1 is irradiated uniformly. Luminescence radiation emitted by fluorescent tumor regions 3 is fed through the same photoconductor 6 and a beam divider 12, e.g., a dichromatic mirror, (FIG. 1) or through a second light conductor 20 (see FIG. 2) to a detector 14 or 25 respectively. These detectors may be, for example, a high sensitivity photomultiplier preceded by filters or photodiodes. If the excitation source is pulsed, a high signal to noise ratio or time resolution spectroscopy is possible, under certain circumstances, with the use of a computer coupled transient recorder.

With the present invention, the use of photochemotherapy on photosensitized, particularly microscopic, multilocularly growing tumors 3 in organ cavities 1 can be improved and simplified considerably. Moreover, in addition to complete tumor detection, the proposed therapy method will generally eliminate the need for anesthesia that could put stress on the patient. Additionally, compared to a theoretically conceivable line-by-line irradiation of all wall sections of the organ cavity 1, the procedure of the present invention appears to shorten the treatment time.

A suitable dispersing medium 4 is, inter alia, a fat emulsion used as a nutrient in intensive care (manufacturer: Kabi Vitrum, Sweden) diluted in physiological saline solution. The use of noncompatible dispersing media 4 which exhibit a dispersing or scattering behavior that, under ceratin circumstances, is more favorable due to wavelength dependency, is possible with the use of transparent balloon catheters 17. A multilayer balloon catheter for multistage dispersion through several layers is also conceivable. The scattering medium 4 consists of scattering centers, e.g., spheres of oil or fat emulsified in water, with a diameter of about the wavelength of the light to be scattered (Different diameters for the excitation- and therapy light). Especially for technical applications, the use of tungsten acid crystals suspended in water or fluorescent dye solutions with an emission wavelength tuned to the absorption wavelength of the, e.g., HpD or the layer to be irradiated is possible. The excitation of this fluorescent dye solution itself easily can be obtained by an adequate light source.

Light conductors 6, 19 and 20 should be standardized and fibers provided which are optimized for homogeneous light distribution. Their ends could be, for example, drawn into points or be spherical. Light conductors 6, 19 and 20 are inserted through special flexible permanent catheters which may possibly be equipped with a fixing device or spacers for the light conductor in the manner of the so-called basket catheters. Rotating light conductors with suitably ground prismatic ends can also be used for the illumination. To homogenize the light beam profile, optical fiber resonators, a mirror having an imbricated structure, a fiber bender, a ground glass plate or combinations thereof are suitable. All these different optical elements 26, schematically shown in FIGS. 1 and 2, are inserted into the fiber optic channels 6 or 19. Parts of FIGS. 1 and 2 may be interchanged, e.g. reference channel formed by elements 12,13 measuring device 16, ballon 17, etc.

It will be understood that the above description of the present invention is susceptible to various modifications, changes and adaptations, and the same are intended to be comprehended within the meaning and range of equivalents of the appended claims.

What is claimed is:

1. A method for the uniform and simultaneous illumination of the interior surface of a cavity by means of radiation for the purpose of observation and/or treatment of the interior surface, comprising the steps of: filling the interior of a cavity, at least in part, with a liquid radiation dispersing medium, and introducing light radiation of a suitable wavelength into said liquid dispersing medium to cause same to substantially uniformly scatter said radition to illuminate said interior surface.

2. A method as defined in claim 1 wherein the cavities are human organ cavities which are irradiated for the purpose of therapy and/or diagnosis and in which existing neoplasms have been previously radiation sensitized by chemical substances.

3. A method as defined in claim 2 wherein said dispersing medium completely fills the cavity.

4. A method as defined in claim 2 wherein said dispersing medium only partially fills the cavity and said step of filling includes inserting a catheter having a transparent balloon on its end into the cavity and introducing said dispersing medium into the balloon to expand same.

5. A method as defined in claim 2 wherein: said radiation is of the absorption wavelength of said substance, and said dispersing medium substantially uniformly reflects said radiation so as to produce toxic reactions in the sensitized regions.

6. A method as defined in claim 2 wherein: said radiation is of the fluorescence excitation wavelength of said substance, and said dispersing medium substantially uniformly reflects said radiation and excites the sensitized regions to emit fluorescence radiation; and further comprising conducting said fluorescent radiation out of the organ cavity for purposes of diagnosis.

7. A method as defined in claim 6 wherein said step of introducing light radiation includes introducing said radiation in the form of light pulses; and further comprising recording a time curve of the fluorescent radiation conducted out of said organ cavity.

8. A method as defined in claim 2 wherein: the organ cavity is a human bladder; and said dispersing medium is a fat emulsion normally used as a nutrient which is diluted with a physiologicl saline solution.

9. A method as defined in claim 1 wherein said step of introducing includes providing a light conductor having one end which has been drawn into a point or sphere; inserting said one end of the light conductor into said dispersing medium within said cavity; and coupling light of said desired wavelength into the other end of said light conductor.

10. A method as defined in claim 9 wherein said step of inserting includes causing said one end of the light conductor to be disposed substantially in the center of said cavity.

11. A method as defined in claim 1 wherein said liquid dispersing medium includes scattering centers with a diameter of substantially said desired wavelength which are suspended in water.

12. A method as defined in claim 11 wherein said dispersing medium is an emulsion of fat or oil and water and said fat or oil forms said scattering centers.

13. A method for the uniform and simultaneous illumination of the interior surface of a cavity by means of light radiation of a desired wavelength for the purpose of observation and/or treatment of the interior surface, comprising the steps of: filling the interior of a cavity, at least in part, with a liquid radiation dispersing medium for radiation of said desired wavelength, and introducing light radiation of said desired wavelength into said liquid dispersing medium to cause same to substantially uniformly scatter said radiation to illuminate said interior surface.

14. A method as defined in claim 13 wherein said step of introducing includes: inserting one end of a light conductor into said dispersing medium within said cavity; and coupling homogenized light of said desired wavelength into the other end of the light conductor.

15. A method as defined in claim 14 wherein said step of inserting includes causing said one end of the light conductor to be disposed substantially in the center of said cavity.

16. A method as defined in claim 14 wherein said one end of light conductor has been drawn into a point or a sphere.

* * * * *